(12) United States Patent
Yoshitome et al.

(10) Patent No.: US 6,531,635 B1
(45) Date of Patent: Mar. 11, 2003

(54) PRECURSORS OF 3-ALKOXYALKANOLS AND PROCESSES FOR THE PREPARATION OF 3-ALKOXYALKANOLS

(75) Inventors: Toshihide Yoshitome, Tokuyama (JP); Hiroshi Kawasaki, Ichihara (JP); Naoya Kawano, Tokuyama (JP)

(73) Assignee: Idemitsu Petrochemicals Co., Ltd., Tokyo (JP)

( * ) Notice: Subject to any disclaimer, the term of this patent is extended or adjusted under 35 U.S.C. 154(b) by 0 days.

(21) Appl. No.: 09/926,549

(22) PCT Filed: May 16, 2000

(86) PCT No.: PCT/JP00/03130

§ 371 (c)(1),
(2), (4) Date: Nov. 19, 2001

(87) PCT Pub. No.: WO00/69799

PCT Pub. Date: Nov. 23, 2000

(30) Foreign Application Priority Data

| May 18, 1999 | (JP) | 11-137027 |
| Jul. 15, 1999 | (JP) | 11-201434 |
| Jul. 15, 1999 | (JP) | 11-201435 |
| Sep. 9, 1999 | (JP) | 11-255400 |

(51) Int. Cl.$^7$ .......... C07C 45/00; C07C 41/00; C07C 27/04
(52) U.S. Cl. .......... 568/465; 568/471; 568/472; 568/689; 568/878; 568/884
(58) Field of Search .......... 568/465, 471, 568/472, 689, 878, 884

(56) References Cited

U.S. PATENT DOCUMENTS 4,446,328 A * 5/1984 Aoshima et al.
5,354,915 A * 10/1994 Reichle 5,892,129 A   4/1999 Hoepp et al.

FOREIGN PATENT DOCUMENTS

| EP | 713851 | 5/1996 |
| JP | 6-72923 | 3/1994 |
| JP | 10-316605 | 12/1998 |
| JP | 2000-72708 | 3/2000 |

OTHER PUBLICATIONS

D. P. Fel'dman, et al., Zh. Obshch. Khim., vol. 65, No., 2, pages 292–296, "Synthesis of 1, 3–Dibromopropane", 1995.

* cited by examiner

*Primary Examiner*—Johann Richter
*Assistant Examiner*—Sikarl A. Witherspoon
(74) *Attorney, Agent, or Firm*—Oblon, Spivak, McClelland, Maier & Neustadt, P.C.

(57) ABSTRACT

Processes for the preparation of 3-alkoxyalkanols useful as solvents for coating materials, photoresists, or the like. Specifically, (1) a process which comprises reacting an α,β-unsaturated aldehyde with an alcohol in the presence of an acidic catalyst and subjecting the obtained product to hydrolysis and hydrogenation successively; (2) a process which comprises subjecting a reaction mixture obtained by the reaction of an α,β-unsaturated aldehyde with an alcohol and comprising the corresponding 1,1,3-trialkoxyalkane and 3-alkoxyalkanal to hydrolysis and hydrogenation at the same time; (3) a process which comprises recovering a 3-alkoxyalkanal through distillation as an azeotropic mixture thereof with water from a reaction solution obtained by the reaction of an alcohol with acid-containing acrolein or methacrolein prepared by the oxidation of propylene or isobutylene, and hydrogenating the recovered 3-alkoxyalkanal into the corresponding 3-alkoxyalkanol; and (4) a process which comprises bringing a gas produced by the oxidation of propylene or isobutylene into contact with an alcohol, conducting the reaction of the gas with the alcohol to form the corresponding 1,1,3-trialkoxyalkane, and subjecting it to hydrolysis and hydrogenation.

16 Claims, No Drawings

PRECURSORS OF 3-ALKOXYALKANOLS AND PROCESSES FOR THE PREPARATION OF 3-ALKOXYALKANOLS

This application is a 371 of PCT/JP00/03130, filed May 16, 2000, now WO00/69799, published Nov. 23, 2000.

TECHNICAL FIELD

The present invention relates to a method for producing 3-alkoxyalkanol precursors, and to a method for producing 3-alkoxyalkanols. More precisely, the invention relates to a method for producing a 3-alkoxyalkanol precursor mixture of 1,1,3-trialkoxyalkane and 3-alkoxyalkanal; to a method for producing a 3-alkoxyalkanal precursor, 1,1,3-trialkoxyalkane; to a method for producing a 3-alkoxyalkanol precursor, 3-alkoxyalkanal; and to a method for producing a 3-alkoxyalkanol.

BACKGROUND ART

For producing 3-alkoxyalkanols such as 3-methoxypropanol, which are useful for solvents for paints and photoresists and for materials for chemical products, heretofore known are <1> a method of reacting trimethylene glycol with a metal followed by reacting the resulting sodium alkoxide with an alkyl halide (J. Am. Chem. Soc., 65, 1276, 1943); <2> a method of reacting 3-chloro-1-propyl alcohol with a metal alkoxide (Japanese Patent Laid-Open No. 113546/1996); and <3> a method of decomposing a diazonium salt obtained from an aminoether (Japanese Patent Laid-Open No. 316605/1998). However, the starting materials for these methods are difficult to obtain, and the practicability of the methods is therefore low.

Another method <4> for which the starting materials are easy to obtain is known. The method comprises hydrogenating a reaction product, which is obtained through reaction of acrolein and methanol in the presence of a basic catalyst, followed by reacting the resulting hydrogenate with acetic acid in the presence of an acid catalyst to give 3-methoxy-1-acetoxypropane (Japanese Patent Laid-Open No. 25821/1995). The patent publication says that the reaction of acrolein with methanol in the presence of a basic catalyst gives a reaction product containing 3-methoxypropylaldehyde, and that the hydrogenation of the reaction product gives a liquid reaction product containing 3-methoxypropanol. However, the method <4> requires a basic catalyst and therefore requires accurate and delicate reaction control. Another drawback of the method is that the yield of 3-alkoxyalkanol therein is low.

The present invention is to solve the drawbacks of the prior-art methods as above, and to provide an efficient and high-yield method for producing 3-alkoxyalkanols and their precursors.

The invention includes four aspects, first to fourth aspects.

The first aspect of the invention is to provide an efficient and high-yield method for producing a 3-alkoxyalkanol precursor mixture of 1,1,3-trialkoxyalkane and 3-alkoxyalkanal. Another object of the first aspect is to provide an efficient and high-yield method for producing a 3-alkoxyalkanol precursor, 3-alkoxyalkanal, from the mixture. Still another object is to provide an efficient and high-yield method for producing the 3-alkoxyalkanol, a final product, from an $\alpha,\beta$-unsaturated aldehyde and an alcohol.

The second aspect of the invention is to provide an industrial method for producing a 3-alkoxyalkanal. Another object of the second aspect is to provide a method for producing a 3-alkoxyalkanol of high purity.

The third aspect of the invention is to provide an industrial method for producing a 3-alkoxyalkanol.

The forth aspect of the invention is to provide an industrial method for producing a 3-alkoxyalkanol of high purity. Another object of the fourth aspect is to provide a method for producing a 1,1,3-trialkoxyalkane and a 3-alkoxyalkanal that give such a 3-alkoxyalkanol.

DISCLOSURE OF THE INVENTION

We, the present inventors have assiduously studied so as to attain the objects of the first aspect of the invention, and, as a result, have found that the objects can be attained by reacting an $\alpha,\beta$-unsaturated aldehyde with an alcohol in the presence of an acid catalyst followed by hydrolyzing the resulting reaction product and then hydrogenating it. On the basis of this finding, we have completed the first aspect of the invention.

To attain the objects of the second aspect of the invention, we, the inventors have assiduously studied on the premise of direct use of oxidized products of propylene or isobutylene, and, as a result, have found that the objects can be attained by distilling a liquid reaction product of acrolein or methacrolein with an alcohol to collect an azeotropic mixture of 3-alkoxyalkanal with water from it, followed by hydrogenating the thus-obtained 3-alkoxyalkanal. On the basis of this finding, we have completed the second aspect of the invention.

To attain the objects of the third aspect of the invention, we, the inventors have specifically noted a step of hydrolysis and a step of hydrogenation of a mixture of 1,1,3-trialkoxyalkane and 3-alkoxyalkanal, and have assiduously studied them. As a result, we have found that the objects can be attained by simultaneously hydrolyzing and hydrogenating the mixture, and, on the basis of this finding, we have completed the third aspect of the invention.

To attain the objects of the fourth aspect of the invention, we, the inventors have specifically noted the treatment of the oxidation product gas of propylene or isobutylene, and have assiduously studied it. As a result, we have found that the objects can be attained by contacting the oxidation product gas of propylene or isobutylene with an alcohol in a specific condition, and, on the basis of this finding, we have completed the fourth aspect of the invention.

Specifically, the present invention provides the following:

(1) A method for producing a mixture of 1,1,3-trialkoxyalkane and 3-alkoxyalkanal, which comprises reacting an $\alpha,\beta$-unsaturated aldehyde with an alcohol in the presence of an acid catalyst;

(2) A method for producing a 3-alkoxyalkanal, which comprises hydrolyzing the mixture produced in the method of above (1);

(3) A method for producing a 3-alkoxyalkanol, which comprises hydrogenating the 3-alkoxyalkanal produced in the method of above (2);

(4) A method for producing a 3-alkoxyalkanal, which comprises distilling a liquid reaction product of acrolein or methacrolein obtained through oxidation of propylene or isobutylene and containing acids, with an alcohol, to thereby collect an azeotropic mixture of a 3-alkoxyalkanal with water;

(5) A method for producing a 3-alkoxyalkanol, which comprises hydrogenating the 3-alkoxyalkanal produced in the method of above (4);

(6) A method for producing a 3-alkoxyalkanol, which comprises simultaneously hydrolyzing and hydrogenating a reaction mixture of 1,1,3-trialkoxyalkane and 3-alkoxyalkanal obtained through reaction of an α,β-unsaturated aldehyde with an alcohol;

(7) A method for producing a 1,1,3-trialkoxyalkane, which comprises reacting acrolein gas or methacrolein gas obtained through contact of an oxidation product gas of propylene or isobutylene with an alcohol capable of almost completely vaporizing in the system, with an alcohol;

(8) A method for producing a 3-alkoxyalkanal, which comprises hydrolyzing the 1,1,3-trialkoxyalkane produced in the method of above (7);

(9) A method for producing a 3-alkoxyalkanol, which comprises hydrogenating the 3-alkoxyalkanal produced in the method of above (8); and

(10) A method for producing a 3-alkoxyalkanol, which comprises simultaneously hydrolyzing and hydrogenating the 1,1,3-trialkoxyalkane produced in the method of above (7).

BEST MODES OF CARRYING OUT THE INVENTION

Embodiments of the invention are described below.

First described is the first aspect of the invention. It includes three embodiments. The first embodiment is a method for producing a mixture of 1,1,3-trialkoxyalkane and 3-alkoxyalkanal, and it comprises reacting an α,β-unsaturated aldehyde with an alcohol in the presence of an acid catalyst.

The acid catalyst to be used in this first aspect is not specifically defined. For this, however, preferred are mineral acids such as sulfuric acid and hydrochloric acid; and solid catalysts such as strong-acidic ion-exchange resins. Of those, especially preferred is a catalyst of strong-acidic ion-exchange resins as the catalyst separation from reaction mixtures is easy.

The amount of the catalyst to be used is not also specifically defined. In general, it falls between 0.0001 and 10 equivalents in terms of acid, but preferably between 0.001 and 1 equivalent, relative to the α,β-unsaturated aldehyde. If the amount is smaller than 0.0001 equivalents, the reaction speed will be low; but if larger than 10 equivalents, it is unfavorable, since such a large amount of the catalyst used could no more augment the intended effect and the catalyst loss increases.

The reaction of the first embodiment may be effected in any mode of flow systems, batch systems or semi-batch systems. The amount of the catalyst to be used in flow-system reaction may be such that the reactants, α,β-unsaturated aldehyde and alcohol are well contacted with the catalyst. Satisfying this condition, the amount of the catalyst for it may be suitably selected from the ordinary range of catalyst amount as above.

The α,β-unsaturated aldehyde to be used in the first aspect of the invention is an aldehyde represented by the following general formula (1):

$$R^1\text{—}CH\text{=}CR^2\text{—}CHO \qquad (1)$$

wherein $R^1$ and $R^2$ each independently indicate a hydrogen atom or an alkyl group. Concretely, preferred examples of the aldehyde are acrolein, methacrolein and crotonaldehyde. The α,β-unsaturated aldehyde may contain water not interfering with its reaction with an alcohol.

The alcohol is not specifically defined, represented by the following general formula (2):

$$R^3\text{—}OH \qquad (2)$$

wherein $R^3$ indicates an alkyl group. Concretely, for example, it includes methanol, ethanol, 1-propanol, isopropanol, 1-butanol, 2-butanol, isobutanol, and t-butanol.

In the first embodiment of the first aspect of the invention, the α,β-unsaturated aldehyde and alcohol both mentioned above are reacted in the presence of the acid catalyst also mentioned above to produce a 3-alkoxyalkanol precursor mixture of 1,1,3-trialkoxyalkane and 3-alkoxyalkanal.

Concretely, for example, produced are a mixture of 1,1,3-trimethoxypropane and 3-methoxypropanal; a mixture of 1,1,3-triethoxypropane and 3-ethoxypropanal; a mixture of 1,1,3-tripropoxypropane and 3-propoxypropanal; a mixture of 1,1,3-triisopropoxypropane and 3-isopropoxypropanal; and a mixture of 1,1,3-trimethoxy-2-methylpropane and 3-methoxy2-methylpropanal.

The condition for the reaction of such an α,β-unsaturated aldehyde and an alcohol is not specifically defined. Regarding the amount of the two to be reacted, the molar ratio of alcohol/α,β-unsaturated aldehyde may fall generally between 1 and 15, but preferably between 3 and 10. If the molar ratio is smaller than 1, heavy matters will be formed and the selectivity of the intended products in this embodiment, 1,1,3-trialkoxyalkane and 3-alkoxyalkanal will decrease. On the other hand, if it is larger than 15, too much alcohol used could no more augment the intended effect, and its loss increases meaninglessly. Using too much alcohol is unfavorable from the economical aspect.

The reaction temperature may fall generally between 0 and 120° C., but preferably between 10 and 100° C. If the reaction temperature is lower than 0° C., the reaction speed will be low; but if higher than 120° C., it is unfavorable, since heavy matters will increase and the selectivity of the intended products will lower.

The reaction finishes within 24 hours, but the time for the reaction preferably falls between 0.1 and 10 hours. If the reaction time is too short, the conversion of the α,β-unsaturated aldehyde will lower; but if too long, it is unfavorable, since side products will increase and the selectivity of the intended 1,1,3-trialkoxyalkane and 3-alkoxyalkanal will lower.

The reaction may be effected under atmospheric pressure or under increased pressure.

The second embodiment of the first aspect of the invention is for producing a 3-alkoxyalkanal by hydrolyzing the reaction mixture produced in the first embodiment thereof.

Precisely, this is a method for converting the 1,1,3-trialkoxyalkane into a 3-alkoxyalkanol precursor, 3-alkoxyalkanal, by hydrolyzing the 3-alkoxyalkanol precursor mixture of 1,1,3-trialkoxyalkane and 3-alkoxyalkanal.

Concretely, 3-methoxypropanal, 3-ethoxypropanal, 3-propoxypropanal, 3-isopropoxypropanal, 3-methoxy-2-methylpropanal and the like are produced in the method.

In this embodiment, the alkoxyalkanol precursor mixture is hydrolyzed while removing alcohol through distillation, whereby almost all the precursor mixture is converted into a 3-alkoxyalkanal. In the step of hydrolysis, it is undesirable to decompose the 3-alkoxyalkanal into the stage of α,β-unsaturated aldehyde. This embodiment is characterized in that the amount of the 3-alkoxyalkanal decomposed into the stage of α,β-aldehyde is reduced.

In the step of hydrolysis, using a catalyst is preferred. The catalyst may be any ordinary acid catalyst for hydrolysis, including, for example, mineral acids such as sulfuric acid and hydrochloric acid, organic acids such as acetic acid, and solid acids such as acidic ion-exchange resins.

The amount of the catalyst to be used is not specifically defined, generally falling between 0.0001 and 10 equivalents interms of acid, but preferably between 0.001 and 1 equivalent, relative to the 1,1,3-trialkoxyalkane. If the amount is smaller than 0.0001 equivalents the hydrolysis speed will be low; but even if larger than 10 equivalents, such a large amount of the catalyst used could no more augment the intended effect of hydrolysis.

The condition for hydrolysis is not also specifically defined. The temperature, the pressure and the time for it may be any ordinary ones.

The temperature may fall generally between 0 and 200° C., but preferably between 10 and 150° C. If it is lower than 0°C., the hydrolysis speed will be low; but if higher than 200° C., it is unfavorable, since the precursor mixture will be decomposed to the stage of α,β-unsaturated aldehyde and the selectivity of the intended 3-alkoxyalkanal will lower.

The hydrolysis finishes within 10 hours, but the time for it is preferably not longer than 5 hours. Too long reaction time for it is unfavorable, since side products will increase and the selectivity of the intended 3-alkoxyalkanal will lower. The amount of water to be present in the reaction zone may well be equivalent or more relative to the 1,1,3-trialkoxyalkane, but is generally up to 20 equivalents. If the amount of water is smaller than the equivalent thereto, the 1,1,3-trialkoxyalkane could not be hydrolyzed sufficiently; but if larger than 20 equivalents, it is unfavorable, since an additional step of post-treating the product for separating water from it will be needed and the step increases the energy costs for the method.

The third embodiment of the first aspect of the invention is for producing a 3-alkoxyalkanol, and it comprises hydrogenating the 3-alkoxyalkanol precursor, 3-alkoxyalkanal produced in the second embodiment mentioned above.

Concretely, this is for producing 3-methoxypropanol, 3-ethoxypropanol, 3-propoxypropanol, 3-isopropoxypropanol, 3-methoxy-2-methylpropanol, etc.

In this step, the 3-alkoxyalkanol precursor is hydrolyzed in the presence of an ordinary hydrogenation catalyst such as Raney nickel, nickel/diatomaceous earth or rhodium/carbon.

The amount of the catalyst to be used is not specifically defined, generally falling between 0.01 and 50% by weight, but preferably between 0.1 and 20% by weight of the 3-alkoxyalkanal. If it is smaller than 0.01% by weight, the hydrogenation speed will be low; but if larger than 50% by weight, it is unfavorable, since such a large amount of the catalyst used could no more augment the intended effect and the catalyst loss increases.

The hydrogenation temperature may fall generally between 20 and 250° C., but preferably between 50 and 180° C. If it is lower than 20° C., the hydrogenation speed will be low; but if higher than 250° C., it is unfavorable, since the precursor will be decomposed and the selectivity of the intended product, 3-alkoxyalkanol will lower.

The pressure may fall generally between 1 and 20 MPa, but preferably between 3 and 15 MPa. If it is lower than 1 MPa, the hydrogenation speed will be low; gut even if higher than 20 MPa, such a high pressure could no more augment the intended effect.

The hydrogenation may be effected in any mode of flow systems, batch systems or semi-batch systems.

Next described is the second aspect of the invention. It includes two embodiments.

The first embodiment of the second aspect of the invention is for producing a 3-alkoxyalkanal, and it comprises distilling a liquid reaction product of acrolein or methacrolein obtained through oxidation of propylene or isobutylene and containing acids, with an alcohol, to thereby collect an azeotropic mixture of a 3-alkoxyalkanal with water.

The propylene or isobutylene oxidation may be effected generally in the presence of a molybdenum-bismuth composite oxide catalyst, at a temperature falling between 280 and 350° C., for a contact time falling between 1.5 and 5.0 seconds, and its reactivity to give acrolein or methacrolein falls between 90 and 97%.

The unit flow yield of acrolein or methacrolein, or that is, the yield thereof in one pass of propylene or isobutylene into the reactor filled with the catalyst falls between 70 and 80%. In general, from 5 to 10% of acids such as acetic acid and acrylic acid are formed as side products in the process of oxidation. Accordingly, the oxidation product contains the acids.

One characteristic feature of this embodiment is that the acrolein or methacrolein produced through the step of oxidation and therefore containing the acids formed as side products in the step is directly reacted with an alcohol in the next step.

The alcohol to be used for the reaction is not specifically defined, including, for example, methanol, ethanol, 1-propanol, isopropanol, 1-butanol, 2-butanol, isobutanol and t-butanol.

In the reaction of acrolein or methacrolein with such an alcohol in this embodiment, generally used is a catalyst.

The catalyst to be used is not specifically defined, including, for example, mineral acids such as sulfuric acid and hydrochloric acid, solid catalysts such as acidic ion exchange resins, as well as basic catalysts such as alkali metals, alkaline earth metals and their hydroxides. Of those, preferred are acidic solid catalysts such as strong-acidic ion-exchange resins, as they are easy to separate and they are stable.

The amount of the catalyst to be used is not also specifically defined, generally falling between 0.0001 and 10 equivalents, but preferably between 0.001 and 1 equivalent relative to acrolein or methacrolein. If it is smaller than 0.0001 equivalents, the reaction speed will be low; but if larger than 10 equivalents, it is unfavorable, since such a large amount of the catalyst used could no more augment the intended effect and the catalyst loss increases.

The reaction of this embodiment may be effected in any mode of flow systems, batch systems or semi-batch systems. The amount of the catalyst to be used in flow-system reaction may be such that the reactants, acrolein or methacrolein and alcohol are well contacted with the catalyst. Satisfying this condition, the amount of the catalyst for it may be suitably selected from the ordinary range of catalyst amount as above.

To the ratio of the two, acrolein or methacrolein and alcohol to be reacted in this embodiment, the same as that for the molar ratio of alcohol/α,β-unsaturated aldehyde in the first embodiment in the first aspect mentioned above may apply for the same reason also mentioned above. To the reaction condition including the reaction temperature, the reaction time and the reaction pressure for this embodiment, the same as those mentioned herein above for the reaction condition for alcohol and α,β-unsaturated aldehyde in the first embodiment of the first aspect mentioned may also apply.

The 3-alkoxyalkanal thus produced in this embodiment includes, for example, 3-methoxypropanal, 3-ethoxypropanal, 3-propoxypropanal, 3-isopropoxypropanal, and 3-methoxy-2-methylpropanal.

As so mentioned hereinabove, the first embodiment of the second aspect of the invention is for distilling the liquid reaction product obtained through reaction of acrolein or methacrolein, which is prepared by oxidizing propylene or isobutylene and therefore contains acids, with an alcohol, to thereby collect an azeotropic mixture of a 3-alkoxyalkanal with water.

Specifically, this is for producing a 3-alkoxyalkanal by distilling the liquid reaction product of such an acid-containing acrolein or methacrolein and an alcohol, in the presence of water to thereby take out an azeotropic mixture of the intended 3-alkoxyalkanal with water through the top of the distillation column.

For this, water may be added to the liquid reaction product obtained through reaction of acrolein or methacrolein with an alcohol, to thereby distill it. For example, in case where propylene is oxidized to give acrolein, the liquid reaction product contains water. In this case, therefore, adding water to the reaction product is unnecessary, and the reaction product may be directly distilled.

The amount of water necessary for the distillation may well be to form the intended azeotropic mixture of a 3-alkoxyalkanal with it. In general, it falls between 2 and 20 equivalents relative to the 3-alkoxyalkanal. If the amount of water is smaller than 2 equivalents, the amount of the 3-alkoxyalkanal to form the azeotropic mixture to be recovered will lower; but if larger than 20 equivalents, it is uneconomical since the distillation column requires an increased number of distillation stages.

The distillation may be effected either under atmospheric pressure or reduced pressure, but is preferably effected under reduced pressure.

The distillation may be effected generally at a temperature not higher than 200° C., but preferably not higher than 150° C. If its temperature is higher than 200° C., it is unfavorable since the 3-alkoxyalkanal will be greatly decomposed into acrolein or methacrolein owing to the influence thereon of the acids existing in the distillation system.

The aqueous azeotropic mixture of 3-alkoxyalkanal collected in the present embodiment does not substantially contain acids. Accordingly, when hydrogenated, it gives high-purity 3-alkoxyalkanol corresponding to it.

The second embodiment of the second aspect of the invention is for producing a 3-alkoxyalkanol by hydrogenating the 3-alkoxyalkanal produced in the first embodiment mentioned above.

For hydrogenating it, the aqueous azeotropic mixture does not require removal of water from it, and it may be directly processed for hydrogenation. In this point, the industrial advantage of the method of this embodiment is obvious.

For the catalyst and its amount to be sued, and also the reaction condition for the hydrogenation in this embodiment, referred to are the same as those mentioned hereinabove for the third embodiment of the first aspect of the invention.

The 3-alkoxyalkanol thus obtained in this embodiment includes, for example, 3-methoxypropanol, 3-ethoxypropanol, 3-propoxypropanol, 3-isopropoxypropanol, and 3-methoxy-2-methylpropanol.

Next described is the third aspect of the invention.

In the third aspect, an $\alpha,\beta$-unsaturated aldehyde is first reacted with an alcohol to prepare a mixture of 1,1,3-trialkoxyalkane and 3-alkoxyalkanal.

The $\alpha,\beta$-unsaturated aldehyde to be used in the third aspect includes, for example, acrolein, methacrolein, and crotonaldehyde. Of those, preferred is acrolein.

The $\alpha,\beta$-unsaturated aldehyde does not require purifying. For it, for example, oxidized gas of propylene may be directly used.

The alcohol for use herein includes, for example, methanol, ethanol, 1-propanol, isopropanol, 1-butanol, 2-butanol, isobutanol, and t-butanol.

In the reaction of such an $\alpha,\beta$-unsaturated aldehyde and an alcohol, generally used is a catalyst.

The catalyst to be used is not specifically defined, and any one mentioned for the first embodiment of the first aspect of the invention is also usable herein. For the amount of the catalyst to be used and the reaction condition for this aspect, referred to are the same as those mentioned hereinabove for the first embodiment of the first aspect of the invention.

In the third aspect of the invention, an $\alpha,\beta$-unsaturated aldehyde such as that mentioned above is reacted with an alcohol mentioned above under the condition also mentioned above to prepare a 3-alkoxyalkanol precursor mixture of 1,1,3-trialkoxyalkane and 3-alkoxyalkanal. Concretely, for the mixture to be prepared herein, referred to are the same as those mentioned hereinabove for the mixture produced in the first embodiment of the first aspect of the invention.

In the third aspect of the invention, the mixture prepared in the manner as above is then hydrolyzed while simultaneously hydrogenated. In other words, the mixture is subjected to simultaneous hydrolysis and hydrogenation in one and the same reaction zone.

For simultaneously hydrolyzing and hydrogenating the mixture, both a catalyst for hydrolysis and a catalyst for hydrogenation are made to exist in the reaction mixture of 1,1,3-trialkoxyalkane and 3-alkoxyalkanal obtained through reaction of the $\alpha,\beta$-unsaturated aldehyde and the alcohol, and the reaction mixture is pressurized with hydrogen in that condition.

For it, a binary catalyst having both the ability of hydrolysis and the ability of hydrogenation may be used.

Through simultaneous hydrolysis and hydrogenation thereof, the 1,1,3-trialkoxyalkane in the mixture is converted into a 3-alkoxyalkanal, and the 3-alkoxyalkanal is immediately converted into a 3-alkoxyalkanol.

For the 3-alkoxyalkanol to be produced in the third aspect of the invention, referred to are the same as those mentioned hereinabove for that to be produced in the third embodiment of the first aspect of the invention.

The catalyst for hydrolysis to be used herein may be the same as that used in the second embodiment of the first aspect mentioned hereinabove. For this, preferred are acidic solid catalysts such as ion-exchange resins as they do not cause plant corrosion.

The catalyst for hydrolysis may be the same as that used in the step of reacting the starting $\alpha,\beta$-unsaturated aldehyde and alcohol, and the catalyst still remaining in the reaction mixture of the $\alpha,\beta$-unsaturated aldehyde and the alcohol may be directly used for it. In this point, the industrial advantage of the method of the invention is remarkable.

The amount of the catalyst to remain in the reaction system is not specifically defined, generally falling between 0.0001 and 10 equivalents, but preferably between 0.001 and 1 equivalent in terms of acid, relative to the 1,1,3-trialkoxyalkane. If it is smaller than 0.0001 equivalents, the reaction speed will be low; but even if larger than 10 equivalents, it will no more augment the intended effect.

The catalyst for hydrogenation may be any ordinary one, including, for example, Raney nickel, nickel/diatomaceous earth, and ruthenium/carbon. For the amount of the catalyst to be used herein, referred to is the same as that mentioned hereinabove for the third embodiment of the first aspect of the invention.

The amount of water to be present in the reaction zone may well be equivalent or more relative to the 1,1,3-trialkoxyalkane, but is generally up to 20 equivalents. If the amount of water is smaller than the equivalent thereto, the 1,1,3-trialkoxyalkane could not be hydrolyzed sufficiently; but if larger than 20 equivalents, it is unfavorable, since an additional step of post-treating the product for separating water from it will be needed and the step increases the energy costs for the method.

The condition for simultaneous hydrolysis and hydrogenation is not specifically defined, but the temperature for it generally falls between 20 and 250° C., preferably between 50 and 180° C. If it is lower than 20° C., the reaction speed will be low; but if higher than 250° C., it is unfavorable, since the selectivity of the intended product, 3-alkoxyalkanol will lower.

For the hydrogen pressure for the reaction, referred to is the same as that mentioned hereinabove for the third embodiment of the first aspect of the invention.

The reaction of hydrolysis and hydrogenation may be effected in any mode of flow systems, batch systems or semi-batch systems.

Next described is the fourth aspect of the invention. It includes four embodiments.

The first embodiment of the fourth aspect of the invention is for producing a 1,1,3-trialkoxyalkane, and it comprises reacting acrolein gas or methacrolein gas obtained through contact of an oxidation product gas of propylene or isobutylene with an alcohol capable of almost completely vaporizing in the system, with an alcohol.

In this, the oxidation of propylene or isobutylene gas is effected generally in the presence of a molybdenum-bismuth composite oxide catalyst, at a temperature falling between 280 and 350° C. for a contact time falling between 1.5 and 5.0 seconds, through which the reaction yield of the product, acrolein or methacrolein falls between 90 and 97%.

The unit flow yield of acrolein or methacrolein falls between 70 and 80%. In general, from 5 to 10% of acids such as acetic acid, acrylic acid and methacrylic acid are formed as side products in the process of oxidation. Accordingly, the oxidation product contains the acids, and may contain any others such as water, nitrogen, oxygen, carbon dioxide and carbon monoxide.

This embodiment is characterized in that the oxidation product gas of propylene or isobutylene is contacted with an alcohol capable of almost completely vaporizing in the system.

The mode of contacting the oxidation product gas with such an alcohol is not specifically defined. Preferably used for it is a column reactor. For example, the oxidation product gas is introduced into it through its bottom, while an alcohol is thereinto through its top, and the two are contacted with each other in a mode of countercurrent flow in the column reactor.

While contacted with an alcohol in such a mode of countercurrent flow, a part or almost all of water in the oxidation product gas and almost all the acids therein are condensed owing to the heat of vaporization of the alcohol, and are then separated from the system.

The alcohol to be fed into the column reactor through its top is not specifically defined. As will be mentioned hereinunder, it is desirable that the alcohol is the same as that to be used in producing the product, 1,1,3-trialkoxyalkane through reaction of acrolein or methacrolein with it.

The alcohol includes, for example, methanol, ethanol, 1-propanol, isopropanol, 1-butanol, 2-butanol, isobutanol, and t-butanol. These alcohols may be used either singly or as combined into their mixture.

The amount of the alcohol to be fed into the column reactor through its top must be such that almost all of it can vaporize when contacted with the oxidation product gas in the reactor. More precisely, the amount of the alcohol must be such that almost all of it can vaporize in the system and that it is enough to condense a part or all of the water existing in the oxidation product gas and almost all the acids existing therein owing to the heat of vaporization of the alcohol.

The amount of the alcohol to be fed into the column reactor through its top is not constant but varies, depending on the water content of the oxidation product gas and also on the amount of the gas. In general, it may fall between 50 g and 5 kg, but preferably between 200 g and 1 kg, relative to 1 m$^3$ of the oxidation product gas.

If the amount of the alcohol fed into the reactor is too small, the acids could not be completely removed from the oxidation product gas; but if too large, it is unfavorable, since the excess alcohol will remain in the bottom of the reactor and the loss alcohol must be recovered.

The alcohol to be fed into the column reactor through its top is preferably pure alcohol, but it may contain minor water not interfering with the process operation. If desired, any other component may be added to the alcohol for any specific object.

For example, for preventing polymerization of acrolein or methacrolein, it is desirable to add a polymerization inhibitor such as hydroquinone to the alcohol.

In that manner, the oxidation product gas of propylene or isobutylene is contacted with such an alcohol capable of almost completely vaporizing in the system, whereby an alcohol-containing acrolein or methacrolein gas is taken out through the top of the reactor and water that contains acids is through the bottom thereof.

In this embodiment, the alcohol-containing acrolein or methacrolein gas is the starting material and this is reacted with an alcohol to produce a 1,1,3-trialkoxyalkane.

The alcohol to be reacted with the acrolein or methacrolein may be, as so mentioned hereinabove, of the same type as that of the alcohol contacted with the oxidation product gas. It includes, for example, methanol, ethanol, 1-propanol, isopropanol, 1-butanol, 2-butanol, isobutanol, and t-butanol.

As in the above, the acrolein or methacrolein gas collected through the top of the column reactor contains the alcohol used for preparing it, and its advantage is that it may be directly processed, as it is, in the next step of reacting it with an alcohol.

In the step of reacting the acrolein or methacrolein with an alcohol, generally used is a catalyst.

The catalyst is not specifically defined, including, for example, mineral acids such as sulfuric acid and hydrochloric acid, solid catalysts such as acidic ion-exchange resins, and basic catalysts such as alkali metals, alkaline earth metals and their hydroxides. For the catalyst, preferred are acidic solid catalysts such as strong-acidic ion-exchange resins, as they are easy to separate and they are stable.

The amount of the catalyst to be used in the step is not also specifically defined, for which, for example, generally referred to are the same as those mentioned hereinabove for the first embodiment of the first aspect of the invention.

For reaction mode and the reaction condition for the step, also referred to are the same as those mentioned hereinabove for the first embodiment of the first aspect of the invention.

The 1,1,3-trialkoxyalkane obtained in the process includes, for example, 1,1,3-trimethoxypropane, 1,1,3-triethoxypropane, 1,1,3-tripropoxypropane, 1,1,3-triisopropoxypropane, and 1,1,3-trimethoxy-2-methylpropane.

The second embodiment of the fourth aspect of the invention is for producing a 3-alkoxyalkanal, and it comprises hydrolyzing the 1,1,3-trialkoxyalkane produced in the above-mentioned first embodiment.

To hydrolyze it, using a catalyst is preferred. For this, referred to are the same as those mentioned hereinabove for the second embodiment of the first aspect of the invention.

For the amount of the catalyst to be used and for the condition for the hydrolysis, also referred to are the same as those mentioned hereinabove for the second embodiment of the first aspect of the invention.

The 3-alkoxyalkanal obtained in the process includes, for example, 3-methoxypropanal, 3-ethoxypropanal, 3-propoxypropanal, 3-isopropoxypropanal, and 3-methoxy-2-methylpropanal.

The third embodiment of the fourth aspect of the invention is for producing a 3-alkoxyalkanol, and it comprises hydrogenating the 3-alkoxyalkanal produced in the above-mentioned second embodiment.

The hydrogenation is effected in the presence of an ordinary hydrogenation catalyst such as Raney nickel, nickel/diatomaceous earth or ruthenium/carbon.

For the amount of the catalyst to be used and for the condition for the hydrogenation, referred to are the same as those mentioned hereinabove for the third embodiment of the first aspect of the invention.

The 3-alkoxyalkanol obtained in the process includes, for example, 3-methoxypropanol, 3-ethoxypropanol, 3-propoxypropanol, 3-isopropoxypropanol, and 3-methoxy-2-methylpropanol.

The fourth embodiment of the fourth aspect of the invention is for producing a 3-alkoxyalkanol, and it comprises simultaneously hydrolyzing and hydrogenating the 1,1,3-trialkoxyalkane produced in the above-mentioned first embodiment.

For simultaneously hydrolyzing and hydrogenating it, the 1,1,3-trialkoxyalkane produced in the first embodiment is processed with water and hydrogen in one and the same reaction zone that contains both a hydrolysis catalyst and a hydrogenation catalyst or contains a binary catalyst having both the ability of hydrolysis and the ability of hydrogenation.

Simultaneously hydrolyzed and hydrogenated in that manner, the 1,1,3-trialkoxyalkane is converted into a 3-alkoxyalkanal corresponding to it, and the resulting 3-alkoxyalkanal is then immediately converted into a 3-alkoxyalkanol corresponding to it.

For the hydrolysis catalyst, herein usable are acid catalysts such as those used in the above-mentioned second embodiment.

The amount of the hydrolysis catalyst to be used is not specifically defined, generally falling between 0.0001 and 10 equivalents, but preferably between 0.001 and 1 equivalent in terms of acid, relative to the 1,1,3-trialkoxyalkane.

If the amount of the catalyst used is smaller than 0.0001 equivalents, the hydrolysis speed will be low; but even if larger than 10 equivalents, such a large amount of the catalyst used could no more augment the intended effect.

For the hydrogenation catalyst, herein usable are those used in the above-mentioned third embodiment.

The amount of the hydrogenation catalyst to be used is not also specifically defined, generally falling between 0.01 and 50% by weight, but preferably between 0.1 and 20% by weight of the 3-alkoxyalkanal.

If the amount of the catalyst used is smaller than 0.01% by weight, the hydrogenation speed will be low; but if larger than 50% by weight, it is unfavorable, since such a large amount of the catalyst used could no more augment the intended effect and the catalyst loss increases.

The amount of water to be present in the reaction zone may well be equivalent or more relative to the 1,1,3-trialkoxyalkane, but is generally up to 20 equivalents. If the amount of water is smaller than the equivalent thereto, the 1,1,3-trialkoxyalkane could not be hydrolyzed sufficiently; but if larger than 20 equivalents, it is unfavorable, since an additional step of post-treating the product for separating water from it will be needed and the step increases the energy costs for the method.

The condition for simultaneous hydrolysis and hydrogenation in the process is not specifically defined. In general, however, the temperature may fall between 20 and 250° C., but preferably between 50 and 180° C. If it is lower than 20° C., the reaction speed will be low; but if higher than 250° C., it is unfavorable, since the selectivity of the intended product, 3-alkoxyalkanol will lower.

The hydrogen pressure may fall generally between 1 and 20 MPa, but preferably between 3 and 15 MPa. If it is lower than 1 MPa, the reaction speed will be low; but even if higher than 20 MPa, such a high pressure could no more augment the intended effect.

EXAMPLES

The invention is described more concretely with reference to the following Examples, which, however, are not intended to restrict the scope of the invention.

Example 1

0.9 g (0.04 equivalents) of a strong-acidic ion-exchange resin (Mitsubishi Chemical's Diaion SK104), 5.6 g (0.1 mols) of acrolein, 19.3 g (0.6 mols) of methanol and 1.8 g (0.1 mols) of water were put into a 100-ml three-neck flask, and reacted with stirring at 50° C. for 5 hours to obtain a liquid reaction product.

The acrolein conversion was 99.8%; the 3-methoxypropanal selectivity was 10 mol %; and the 1,1,3-trimethoxypropane selectivity was 80 mol %. The conversion and the selectivity were obtained through gas chromatography (GC).

In the following Examples, Comparative Examples and Reference Examples, the conversion, the selectivity, the degree of hydrolysis and the purity were obtained through GC.

Example 2

Subsequently to the process of Example 1, 9 g (0.5 mols) of water was added to the liquid reaction product of Example 1, while the strong-acidic ion-exchange resin was left as it was, and 1,1,3-trimethoxypropane therein was hydrolyzed under reduced pressure (6.7 kPa) while the reaction system was kept at 25 to 36° C. and while 78% of methanol was evaporated away. Thus hydrolyzed, the essential ingredient of the product was 3-methoxypropanal.

The degree of hydrolysis was 99 mol %; and those having been decomposed to acrolein amounted to 4 mol % of the total of 1,1,3-trimethoxypropane and 3-methoxypropanal.

Example 3

The hydrolyzed product of Example 2 was filtered to remove the strong-acidic ion-exchange resin, and then transferred into an autoclave. With 2% by weight, relative to 3-methoxypropanal, of Raney nickel being added thereto, this was hydrogenated under a hydrogen pressure of 5 MPa at 80° C. for 3 hours.

In this, 3-methoxypropanal was almost completely hydrogenated, and the overall yield of 3-methoxypropanol in the process was 85 mol % relative to the starting compound, acrolein.

Example 4

0.9 g (0.04 equivalents) of a strong-acidic ion-exchange resin (Mitsubishi Chemical's Diaion SK104), 5.6 g (0.1 mols) of acrolein, 27.6 g (0.6 mols) of ethanol and 1.8 g (0.1 mols) of water were put into a 100-ml three-neck flask, and reacted with stirring at 50° C. for 8 hours.

The acrolein conversion was 96.7%; the 3-ethoxypropanal selectivity was 32 mol %; and the 1,1,3-triethoxypropane selectivity was 55 mol %.

Example 5

Subsequently to the process of Example 4, 9 g (0.5 mols) of water was added to the liquid reaction product of Example 4, while the strong-acidic ion-exchange resin was left as it was, and 1,1,3-triethoxypropane therein was hydrolyzed under reduced pressure (6.7 kPa) while the reaction system was kept at about 40° C. and while 78% of ethanol was evaporated away. Thus hydrolyzed, the essential ingredient of the product was 3-ethoxypropanal.

The degree of hydrolysis was 98 mol %; and those having been decomposed to acrolein amounted to 3 mol % of the total of 1,1,3-triethoxypropane and 3-ethoxypropanal.

Example 6

The hydrolyzed product of Example 5 was filtered to remove the strong-acidic ion-exchange resin, and then transferred into an autoclave. With 2% by weight, relative to 3-ethoxypropanal, of Raney nickel being added thereto, this was hydrogenated under a hydrogen pressure of 5 MPa at 80° C. for 3 hours.

In this, 3-ethoxypropanal was almost completely hydrogenated, and the overall yield of 3-ethoxypropanol in the process was 80 mol % relative to the starting compound, acrolein.

Comparative Example 1

48.2 g (this corresponds to 1.5 mols of methanol) of methanol that contained 5 ml of 0.1 N sodium hydroxide/methanol solution (the amount of sodium hydroxide is 0.0005 mols) was put into a 200-ml four-neck flask, and cooled to 0 C. To this, dropwise added was 28 g (0.5 mols) of acrolein over a period of 30 minutes while the temperature of the reaction liquid was kept at 2 to 6° C. Next, the liquid reaction product was neutralized with acetic acid to terminate the reaction.

The acrolein conversion was 99.2%; and the 3-methoxypropanal selectivity was 69%. Except 3-methoxypropanal, the products were acrolein dimer and trimer, and methanol adducts to these. The composition of the liquid reaction product obtained herein completely differed from that of the liquid reaction product of Example 1.

Next, the liquid reaction product was transferred into an autoclave. With 2% by weight, relative to 3-methoxypropanal, of Raney nickel being added thereto, this was hydrogenated under a hydrogen pressure of 5 MPa at 80° C. for 3 hours.

As a result, 3-methoxypropanal in this was completely hydrogenated. The overall yield of 3-methoxypropanol thus obtained was 68 mol % relative to the starting compound, acrolein.

Example 7

96 g (3 mols) of methanol and 5 g (0.04 equivalents) of a strong-acidic ion-exchange resin catalyst (Mitsubishi Chemical's Diaion SK104) were put into a glass reactor, and kept at 50° C.

Next, 233 g (this contains 0.5 mols of acrolein) of an acrolein gas mixture (comprising 12.0 wt. % of acrolein, 1.8 wt. % of acrylic acid, 0.1 wt. % of acetic acid and 10 wt. % of water) that had been taken out of a process line of producing acrylic acid in a method of direct oxidation of acrolein was gradually introduced into the reactor, and reacted therein for 5 hours.

After the reaction, methanol and other light matters were removed from it through distillation while the catalyst was still left therein. The thus-obtained liquid reaction product of 3-methoxypropanal contained acrylic acid and acetic acid.

The 3-methoxypropanal yield was 85 mol % relative to acrolein.

The catalyst was removed through filtration, and the resulting liquid reaction product containing 3-methoxypropanal, acetic acid and acrylic acid was distilled in a precision distillation device under a reduced pressure of 13.3 kPa. An azeotropic distillate of 3-methoxypropanal with water was taken out through the top of the distillation column. In this stage, the temperature of the column top fell between 46 and 47° C.

The amount of 3-methoxypropanal in the azeotropic mixture was 64% by weight, and acetic acid and acrylic acid were detected little therein.

Example 8

The azeotropic distillate in Example 7 was put into an autoclave, and 2% by weight, relative to 3-methoxypropanal, of ruthenium/carbon was added thereto. With hydrogen introduced thereinto, this was hydrogenated under a pressure of 5 MPa for 3 hours. The hydrogenation went on almost stoichiometrically.

The resulting liquid hydrogenation product was distilled in a precision distillation device to obtain 3-methoxypropanol. The purity of the product, 3-methoxypropanol was 99% or more.

Comparative Example 2

The liquid reaction product of 3-methoxypropanal, which had been obtained in the process of Example 7 and contained acrylic acid and acetic acid, was hydrogenated in the same manner as in Example 8. In this, however, the liquid reaction product was not distilled prior to the hydrogenation.

After hydrogenated, this was distilled in a precision distillation device to obtain a fraction of 3-methoxypropanol. However, the thus-fractionated 3-methoxypropanol contained acetic acid, propionic acid, 3-methoxypropyl acetate and 3-methoxypropyl propionate, and its purity was 88% and was low.

Example 9

25 g (0.04 equivalents) of a strong-acidic ion-exchange resin (Mitsubishi Chemical's Diaion SK104), 11.2 g (0.2 mols) of acrolein, 38.5 g (1.2 mols) of methanol and 3.6 g (0.2 mols) of water were put into a 100-ml three-neck flask, and reacted with stirring at 50° C. for 5 hours to obtain a mixture of, 1,1,3-trimethoxypropane and 3-methoxypropanal.

The acrolein conversion was 99.2%; the 1,1,3-trimethoxypropane selectivity was 72%; and the 3-methoxypropanal selectivity was 22%.

The reaction mixture was transferred into an autoclave with the strong-acidic ion-exchange resin being left therein, and 5% by weight, relative to the total of 1,1,3- trimethoxypropane and 3-methoxypropanal, of Raney nickel was added thereto. With that, this was hydrogenated under a hydrogen pressure of 5 MPa at 80° C. for 4 hours.

The catalyst was removed from it through filtration, and the hydrogenated product was analyzed through gas chromatography (GC). The yield of 3-methoxypropanol was 93 mol % relative to acrolein.

The result indicates that 1,1,3-trimethoxypropane was stoichiometrically hydrolyzed into 3-methoxypropanal, and 3-methoxypropanal was also stoichiometrically hydrogenated into 3-methoxypropanol.

Comparative Example 3

A reaction mixture of 1,1,3-trimethoxypropane and 3-methoxypropanal was prepared in the same manner as in Example 9.

After the catalyst was removed from it through filtration, the reaction mixture was hydrogenated in the same manner as in Example 9. The hydrogenated mixture was analyzed through GC, and it confirmed that all of 1,1,3-trimethoxypropane still remained as it was in the mixture.

Example 10

Propylene was directly oxidized in the presence of a molybdenum-bismuth catalyst at 350° C. for 2 seconds to obtain an acrolein-containing gas. This comprised 7.2 mol % of acrolein, 17.9 mol % of water, 0.7 mol % of acrylic acid, 0.06 mol % of acetic acid, and contained 74.1 mol % of other matters, nitrogen, oxygen, carbon dioxide and carbon monoxide.

The acrolein-containing gas (245° C.) was fed into a gas absorption column filled with Raschig rings corresponding to 5 stages, at a flow rate of 66 Nl/hr through the bottom of the column.

Through its top, 0.01 wt. % hydroquinone-containing methanol at 30° C. was fed into the column, at a flow rate of 30 g/hr.

As a result, a methanol-containing acrolein gas was taken out of the top of the column, and a liquid containing acids was out of the bottom thereof.

Acids were detected little in the methanol-containing gas taken out of the top of the column. Entirely vaporized, almost all of methanol fed into the column was recovered through the top of the column.

Next, the gas thus taken out through the column top was jetted into a methanol solution containing a strong-acidic ion-exchange resin, and reacted for 5 hours at a preset temperature of 50° C. The reaction liquid was analyzed. The acrolein conversion was 99%, and the 1,1,3-trimethoxypropane selectivity was 80 mol %.

Example 11

The 1,1,3-trimethoxypropane-containing reaction liquid obtained in Example 10 was, while the strong-acidic ion exchange resin was left as it was therein, hydrolyzed under a reduced pressure of 6.7 kPa at 30° C. while methanol was evaporated away. After thus hydrolyzed, this contained 3-methoxypropanal.

The degree of hydrolysis of 1,1,3-trimethoxypropane into 3-methoxypropanal was 99 mol %.

Example 12

The 3-methoxypropanal-containing reaction liquid obtained in Example 11 was filtered to remove the strong-acidic ion-exchange resin from it, and 2% by weight, relative to 3-methoxypropanal therein, of Raney nickel was added thereto. With that, this was hydrogenated under a hydrogen pressure of 5 MPa at 80° C. for 3 hours.

After thus hydrogenated, the reaction liquid was filtered to remove the catalyst from it, and this was distilled in a precision distillation device to isolate 3-methoxypropanol.

In this process, 3-methoxypropanal was almost completely hydrogenated, and the purity of the product, 3-methoxypropanol was 99% or more.

Example 13

To the 1,1,3-trimethoxypropane-containing reaction liquid obtained in Example 10 and still containing the strong-acidic ion-exchange resin therein, added was 2% by weight, relative to 1,1,3-trimethoxypropane therein, of Raney nickel, and this was simultaneously hydrolyzed and hydrogenated under a hydrogen pressure of 5 MPa at 80° C. for 3 hours in one and the same reactor.

In this process, 1,1,3-trimethoxypropane was almost stoichiometrically hydrolyzed and hydrogenated, and the resulting reaction mixture was distilled in a precision distillation device. The product, 3-methoxypropanol thus obtained in the process had a purity of 99% or more.

Reference Example 1

In the presence of a molybdenum-bismuth catalyst, propylene was directly oxidized to obtain an acrolein-containing gas. This comprised 7.2 mol % of acrolein, 17.9 mol % of water, 0.7 mol % of acrylic acid, 0.06 mol % of acetic acid, and contained 74.1 mol % of other matters, nitrogen, oxygen, carbon dioxide and carbon monoxide.

The acrolein-containing gas (245° C.) was cooled, then jetted into a methanol solution that contained a strong-acidic ion-exchange resin, and reacted for 5 hours at a preset temperature of 50° C.

The acrolein conversion was 99%, and the 1,1,3-trimethoxypropane selectivity was 80 mol %.

To the reaction liquid that still contained the strong-acidic ion-exchange resin therein, added was 2% by weight, relative to 1,1,3-trimethoxypropane therein, of ruthenium/carbon, and this was simultaneously hydrolyzed and hydrogenated under a hydrogen pressure of 5 MPa at 80° C. for 3 hours in one and the same reactor.

The reaction mixture was then distilled in a precision distillation device to isolate 3-methoxypropanol from it. However, the product, 3-methoxypropanol contained impurities of propionic acid and methoxypropyl propionate, and its purity was 94% and was low.

INDUSTRIAL APPLICABILITY

According to the first aspect of the invention, there are provided a method for producing a 3-alkoxyalkanol precursor mixture capable of giving a good yield of 3-alkoxyalkanol useful for various solvents, a method for producing a 3-alkoxyalkanol precursor, and a method for producing a 3-alkoxyalkanol.

According to the second aspect of the invention, there are provided an industrial method for producing a 3-alkoxyalkanol precursor, 3-alkoxyalkanal, and a method for producing a 3-alkoxyalkanol of high purity which is useful for solvents for paints, photoresists and others and for materials for chemical products.

According to the third aspect of the invention, there is provided an industrial method for producing a 3-alkoxyalkanol in a simplified manner.

According to the fourth aspect of the invention, there are provided a method for producing a 3-alkoxyalkanol of high purity which is useful for various solvents and others, and a method for producing 3-alkoxyalkanol precursors, 3-alkoxyalkanal and 1,1,3-trialkoxyalkane, which give such a 3-alkoxyalkanol of high purity.

The industrial advantages of the invention in various fields of, for example, solvent production and others are significant.

What is claimed is:

1. A method for producing a 3-alkoxyalkanol, comprising: simultaneously hydrolyzing and hydrogenating a reaction mixture of 1,1,3-trialkoxyalkane and 3-alkoxyalkanal obtained through reaction of an $\alpha,\beta$-unsaturated aldehyde with an alcohol.

2. The method for producing a 3-alkoxyalkanol of claim 1, wherein the $\alpha,\beta$-unsaturated aldehyde is acrolein.

3. A method for producing a 3-alkoxyalkanol, comprising: simultaneously hydrolyzing and hydrogenating the 1,1,3-trialkoxyalkane produced by a method comprising:
    reacting an oxidation product gas of propylene or isobutylene, which comprises acrolein gas or methacrolein gas, with an alcohol capable of almost completely vaporizing in the system with an alcohol.

4. The method of claim 1, wherein said 3-alkoxyalkanol is 3-methoxypropanol.

5. The method of claim 1, wherein said 3-alkoxyalkanol is 3-ethoxypropanol.

6. The method of claim 1, wherein said 3-alkoxyalkanol is 3-propoxypropanol.

7. The method of claim 1, wherein said 3-alkoxyalkanol is 3-isopropoxypropanol.

8. The method of claim 1, wherein said 3-alkoxyalkanol is 3-methoxy-2-methylpropanol.

9. The method of claim 1, comprising hydrogenating said reaction mixture using a catalyst.

10. The method of claim 9, wherein said catalyst is Raney nickel, nickel/diatomaceous earth or ruthenium/carbon.

11. The method of claim 9, wherein the amount of said catalyst ranges between 0.1 to 20% by weight of the 3-alkoxyalkanal.

12. The method of claim 1, wherein said hydrogenation is carried out at a pressure ranging from 1 to 20 Mpa.

13. The method of claim 1, wherein said hydrogenation is carried out at a pressure ranging from 3 to 15 Mpa.

14. The method of claim 1, wherein said simultaneous hydrolysis and hydrogenation is carried out at a temperature ranging from 20 to 250° C.

15. The method of claim 1, wherein said simultaneous hydrolysis and hydrogenation is carried out at a temperature ranging from 50 to 180° C.

16. The method of claim 1, wherein said simultaneous hydrolysis and hydrogenation is carried out in the presence of from 1 to 20 equivalents of water relative to the 1,1,3-trialkoxyalkane.

* * * * *

UNITED STATES PATENT AND TRADEMARK OFFICE
CERTIFICATE OF CORRECTION

PATENT NO. : 6,531,635 B1
DATED : March 11, 2003
INVENTOR(S) : Yoshitome et al.

It is certified that error appears in the above-identified patent and that said Letters Patent is hereby corrected as shown below:

<u>Title page,</u>
Item [73], Assignee, should read:

-- [73] Assignee: Idemitsu Petrochemical Co., Ltd.,
　　　　　　　　　Tokyo (JP) --

Signed and Sealed this

Twenty-second Day of July, 2003

JAMES E. ROGAN
*Director of the United States Patent and Trademark Office*